United States Patent [19]
Gu et al.

[11] Patent Number: 6,133,021
[45] Date of Patent: Oct. 17, 2000

[54] BIOREACTOR SYSTEM AND METHOD FOR PROBING TOXIC MATERIALS

[75] Inventors: Man Bock Gu, Kwangju; Joong Hyun Kim, Tongyoung, both of Rep. of Korea

[73] Assignee: Kwangju Institute of Science and Technology, Rep. of Korea

[21] Appl. No.: 09/212,740

[22] Filed: Dec. 15, 1998

[51] Int. Cl.[7] .................................................. C12M 1/34
[52] U.S. Cl. ...................... 435/288.7; 435/808; 435/849
[58] Field of Search ........................... 422/82.05, 82.06, 422/82.09; 435/287.1, 288.7, 808, 849

[56] References Cited

U.S. PATENT DOCUMENTS 5,441,873  8/1995  Knight et al. ............................. 435/34
5,840,572  11/1998 Copeland et al. ..................... 435/286.7

OTHER PUBLICATIONS

K. W. Schramm, A. Kaune, B. Beck, W. Thumm, A. Behechti, A Kettrup, P. Nickolova; Acute Toxicities of Five Nitromusk Compounds in Daphnia, Algae and Photoluminescent Bacteria; Wat. Res. vol. 30, No. 10, pp. 2247–2250; Apr. 1996.

S.A.L.M. Kooijman, J.J.M. Bedaux; Analysis of Toxicity Tests on Daphnia Survival and Reproduction; Wat. Res. vol. 30, No. 7, pp. 1711–1723; Feb. 1996.

Leonard I. Sweet, David F. Tracers, Peter G. Meier; Chronic Toxicity Evaluation of Wastewater Treatment Plant Effluents with Bioluminescent Bacteria: A Comparison with Invertebrates and Fish; Environmental Toxicology and Chemistry, vol. 16, No. 10, pp. 2187–2189; Apr. 11, 1997.

Mikio Kikuchi, Meiko Wakabayashi; Monitoring the Biological Effects of Chemicals in River Water using *Daphnia magna*; pp. 627–633; 1997.

*Primary Examiner*—David A. Redding
*Attorney, Agent, or Firm*—Hickman Coleman & Hughes, LLP

[57] ABSTRACT

A bioreactor system of probing toxic materials using microorganisms comprises two reactors. A first-step reactor serves as a microorganism reservoir in which the microorganisms are continuously cultured in a constant phase and a second-step reactor, provided with fiber optics, offers a place in which the microorganisms meet the toxic materials for the first time. Since the microorganisms are so genetically recombinant as to luminesce upon reaction with toxic materials, light is generated in the second-step reactor and, then, transmitted along the fiber optics to a luminometer where the change in the intensity of the light is monitored over time. The microorganisms can be stably provided from the reservoir, so that it is possible to continuously monitor the light intensity and thus, to trace the pollution of the toxic materials. The toxic materials may come from any of the sources including rivers, waste water, sewage, agricultural and industrial water, household water, tap water, atomic power plants, etc.

8 Claims, 4 Drawing Sheets

BIOREACTOR SYSTEM AND METHOD FOR PROBING TOXIC MATERIALS

BACKGROUND OF THE INVENTION

1. Field of the Invention

The present invention relates to a bioreactor system of and a method for probing toxic materials and, more particularly, to a bioreactor system capable of monitoring the pollution of toxic materials continuously and economically and a method for probing toxic materials by use of the system.

2. Description of the Prior Art

The pollution or toxicity of the water in, for example, rivers, sources of water supply, and waste water disposal plants has been classified by the kinds of the aquatic organisms, such as water flea and fishes, to live therein.

In order for this conventional technique to be valid, the extent to which toxic chemicals or materials affect the aquatic organisms must first be determined. On the basis of this determination, introduction and toxicity levels of toxic materials can be decided. Accordingly, it takes a great deal of time to probe the toxicity of water with the technique of utilizing the aquatic organisms. Further, in the conventional technique it is difficult to continuously detect various toxic materials.

Recently, active research has been directed to utilizing microorganisms in probing toxicity of water, which have advantages over the aquatic organisms. For instance, there advantages over the aquatic organisms. For instance, there were developed genetically-recombinant bacteria which are able to emit biological light according to the kinds of toxic materials. Where the bacteria are used for a long time to determine whether toxic materials are introduced into the water of waste water treatment plants, rivers, or sources of water supply, a large quantity of nutrient media are required for their growth and maintenance. The presence of a large quantity of toxic materials inhibits the growth of the microorganisms, resulting in inability to probe toxicity of water.

SUMMARY OF THE INVENTION

Therefore, it is an object of the present invention to overcome the above problems encountered in prior arts and to provide a bioreactor system of probing toxic materials, which is continuously operable.

It is another object of the present invention to provide the bioreactor system which can detect various toxic materials.

It is a further object of the present invention to provide the bioreactor system which is economically favorable.

It is still a further object of the present invention to provide a method for probing toxic materials by use of the system.

In an aspect of the present invention, there is provided a bioreactor system for probing toxic materials using microorganisms, which comprises a first-step reactor serving as a microorganism reservoir in which the microorganisms are continuously cultured in a constant phase, and a second-step reactor provided with fiber optics, offering a place in which the microorganisms meet the toxic materials for the first time and emit light which is transmitted along the fiber optics to a luminometer, the microorganisms being so genetically recombinant as to luminesce upon reaction with the toxic materials.

In another aspect of the present invent, there is provided a method for probing toxic materials, comprising the steps of: culturing and maintaining microorganisms in a certain phase in a first-step reactor, said microorganisms being adapted to luminesce upon reaction with toxic materials; providing the culture to a second-step reactor; adding toxic materials at a predetermined concentration in the second-step reactor; detecting the light emitted from the microorganisms by fiber optics; and monitoring the change of the light with time by a luminometer.

According to the system, the microorganisms can be stably provided from the reservoir, so that it is possible to continuously monitor the light intensity and thus, to pursue the pollution of the toxic materials. The toxic materials may come from any of the sources including rivers, waste water, sewage, agricultural and industrial water, household water, tap water, atomic power plants, etc.

BRIEF DESCRIPTION OF THE DRAWINGS

The above and other objects and aspects of the invention will become apparent from the following description of embodiments with reference to the accompanying drawings in which.

DETAILED DESCRIPTION OF THE INVENTION

The application of the preferred embodiments of the present invention is best understood with reference to the accompanying drawings.

Figure 1:
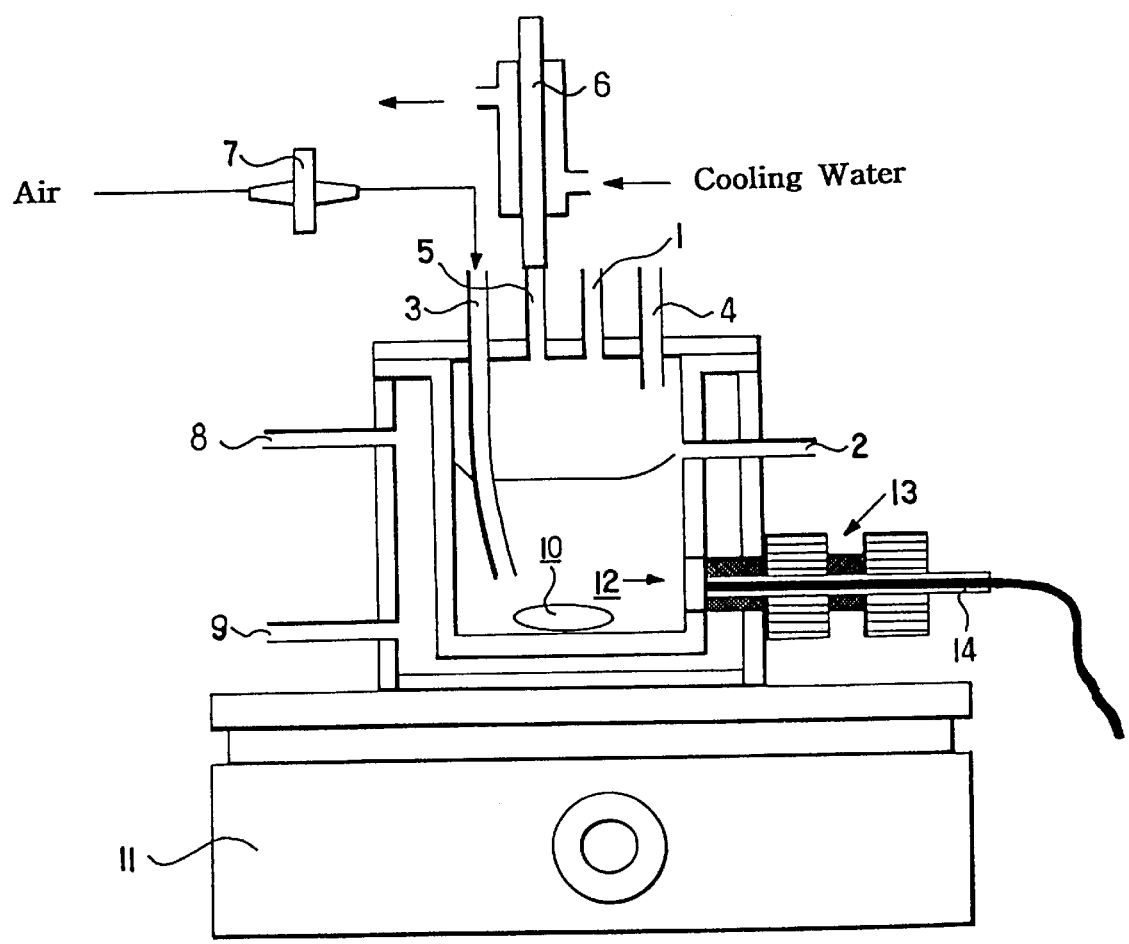
FIG. 1 is a schematic view showing a bioreactor in which microorganisms are grown and meet with toxic materials to emit light which is transmitted along fiber optics to a luminometer.

First, referring to FIG. 1, there is a small bioreactor equipped with fiber optics. It comprises a culture bath in which microorganisms are grown. For the growth, a fresh culture medium is fed to the bath via an inlet 1 and the used medium is drained via an outlet 2. In the case that the bacteria are aerobic, the air is introduced via an air conduit 3, but must be previously filtered through an air filter 7 in order for the medium not to be contaminated by other microorganisms. The tank is also provided with a drop 4 through which an inoculum and toxic materials are added to the medium. During culturing, a small quantity of gas, such as carbon dioxide, is generated and discharged out along a gas pipe 5 connected to a condenser where the gas is condensed by cold water. The bioreactor is maintained at 30° C. with the aid of a double jacket which is connected to a warm water supply via a water inlet 9 and a water outlet 8 for circulating warm water. In the culture tank, a magnetic bar 10 is rotated according to a rotational magnetic field of a magnetic stirring plate 11, so as to stir the culture medium.

In accordance with the present invention, the microorganisms are adapted to emit light when they are in contact with toxic materials. This light emitted from the microorganisms is detected by fiber optics 14 (i.e. Fiber Optic Probe 20-040 from Turner Designs) which are provided at a window 12 set in a lower portion of the tank. This biological light is then transmitted to a luminometer (e.g. Turner Designs Model 20e) without any loss, along the fiber optics 14 which are associated with a fixing means 13.

The bioreactor system of probing toxic materials may be of any size if it is operable. Economically favorable is a small one having an operation volume of, for example, 38 ml, 20 ml, or 10 ml.

Figure 2:
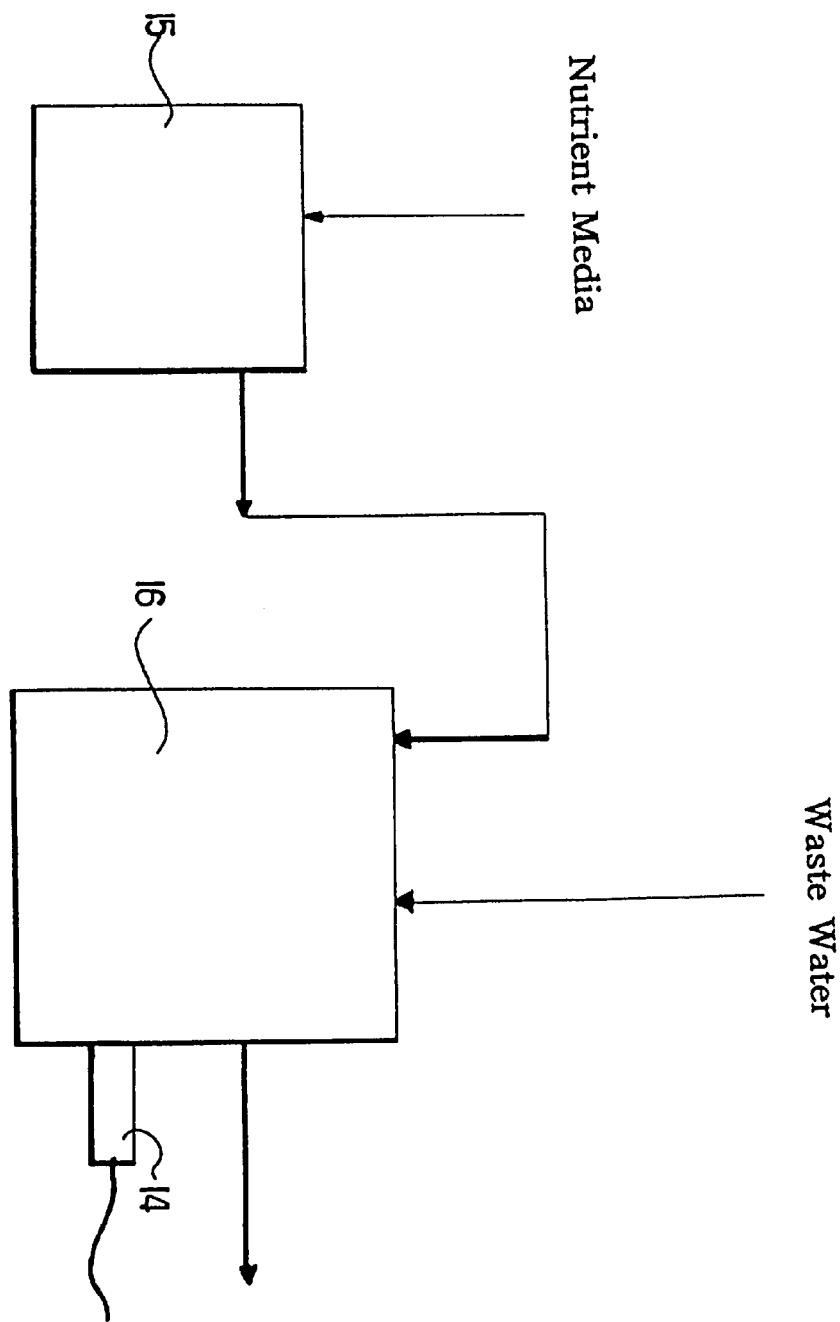
FIG. 2 is a schematic diagram showing the bioreactor system consisting of two reactors, in accordance with the present invention.

With reference to FIG. 2, there is schematically shown a system for continuously probing the toxic materials contained in water. As seen, it consists of two bioreactors 15 and 16, the latter being provided with fiber optics 14. In the first-step bioreactor 15, the microorganisms are grown to a lag phase with the fresh culture medium being continuously fed. Since they are brought into contact with no toxic materials, they can be constantly maintained at the phase in the first-step reactor 15. Some of the culture in the first-step bioreactor 15 is introduced into the second-step bioreactor 16 where the microorganisms meet the waste water from waste water plants, rivers, sources of-water supply, atomic power plants, etc. Since the microorganisms are genetically engineered to emit light upon reaction with toxic chemicals, there may be a high or low intensity of light depending on the amounts of the toxic chemicals present in the waste water.

The light emitted from the microorganisms in the second-step bioreactor is transmitted along the fiber optics 14 to a luminometer where the intensity of the light is continuously monitored over time to determine the amount of toxic materials.

In an economical aspect, the bioreactors preferably have small operation volumes. For example, the first-step bioreactor 15 and the second-step bioreactor 16 may be 10 ml and 20 ml in operation volume, respectively.

When microorganisms, even if they are adapted to probe toxicity, are exposed to toxic materials for an extended period of time, their growth is inhibited. Thus, it is virtually impossible for microorganisms to continuously probe toxicity over an extended period of time. In the present invention, this can be overcome by using the two-step bioreactor system. That is, the first-step bioreactor is used to sustain the microorganisms in a lag phase and plays the role of a reservoir to supply the microorganisms to the second-step bioreactor. Since they meet the toxic materials to be probed, for the first time in the second-step bioreactor and supplemented from the reservoir, continuously probing is possible over an extended period of time. Light is generated when the microorganisms are influenced by the toxic materials and its intensity is modulated over time. The light intensity which is being modulated is transmitted along the fiber optics to a luminometer without loss. Therefore, the bioreactor according to the present invention can be used to quickly and continuously probe the presence or absence of toxic materials in aqueous solutions and thus, can be applied for various uses, for example, for determining to what extent waste water is cleanly treated in waste water treatment plants, monitoring whether toxic materials are introduced into rivers, detecting whether the waste water from an atomic power plant is polluted with radioactive materials, etc.

The system of the present invention is advantageously made to be small in operation volume. The advantages of the small operation volume can be exemplified by low consumption amount of a nutrient medium to be needed to grow the microorganisms, low cost for manufacturing the system, and ease in operating and handling the system.

In the present invention, *E. coli* TV1061 (ATCC 69315) which emits light when its proteins are deformed or destroyed, is employed as a probe for detecting the toxic materials which do such damage. Phenols are typical of the toxic materials.

A better understanding of the present invention may be obtained in light of following examples which are set forth to illustrate, but are not to be construed to limit, the present invention.

EXAMPLE I

*E. coli* TV1061 was continuously grown at a dilution rate in a bioreactor which was equipped with fiber optics and had an operation volume of 38 ml. When phenol was introduced in the bioreactor to give a total concentration of 300 ppm, the biological light emitted from the *E. coli* was measured by a luminometer.

Figure 3:
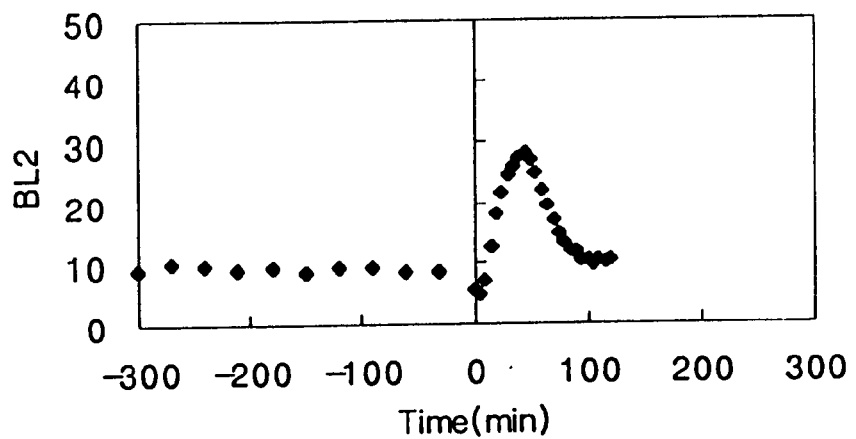
FIG. 3 is a luminosity curve in which the intensity of the biological light emitted from microorganisms is plotted with respect to times when a dilution rate is 0.76/hr for the first-step reactor and 0.7/hr for the second-step reactor.
Figure 4:
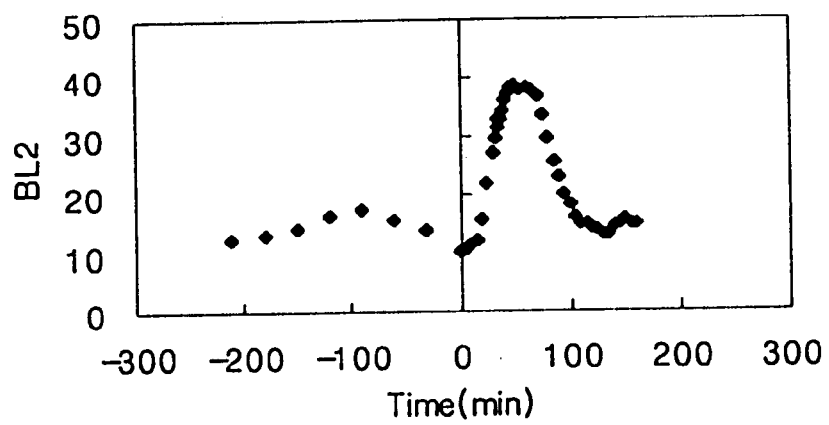
FIG. 4 is a luminosity curve in which the intensity of the biological light emitted from microorganisms is plotted with respect to times when a dilution rate is 0.76/hr for the first-step reactor and 1.1/hr for the second-step reactor.

The biological light (BL) measurements at a dilution rate of 0.7/hr and 1.9/hr are shown in FIGS. 3 and 4, respectively. As shown in FIGS. 3 and 4, 300 ppm of phenol can be probed in 60 min.

EXAMPLE II

A two-step bioreactor system consisting of a first tank with an operation volume of 100 ml and a second tank with an operation volume of 20 ml, was used. The dilution rate was 0.83/hr for both tanks. *E. coli* TV1061 was continuously cultured for more than 100 hours while phenol was added in the second tank to final concentrations of 100 ppm, 300 ppm, 700 ppm and 1,400 ppm at predetermined times.

Figure 5:
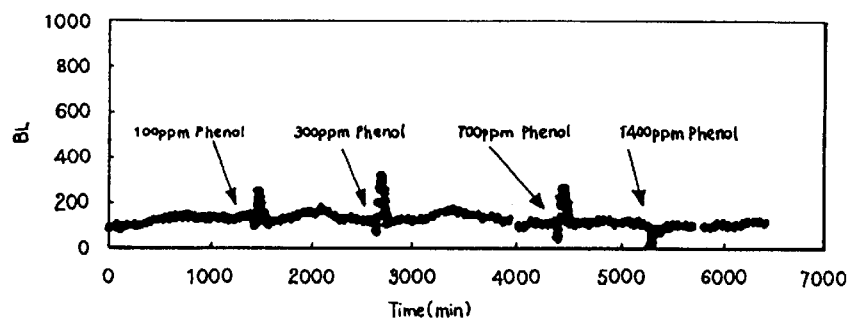
FIG. 5 is a continuous luminosity curve showing the intensity change of the biological light with phenol concentrations over times when a dilution rate is 0.83/hr for both bioreactors.
Figure 6:
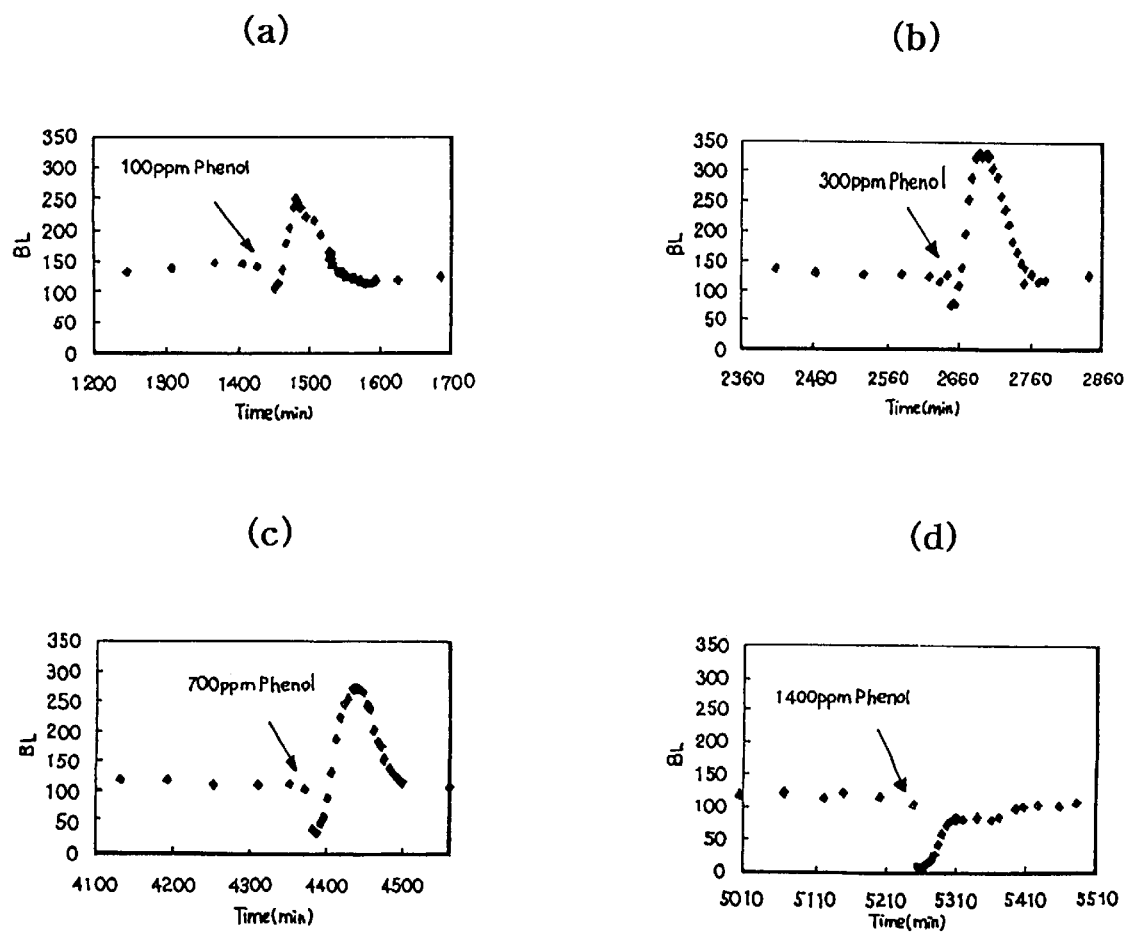
FIGS. 6a to 6d are luminosity curves corresponding to the respective phenol concentrations of FIG. 5.

The biological light was measured and its intensities were plotted with respect to times in FIGS. 5 and 6. FIG. 5 shows the overall procedure while FIGS. 6a to 6d each show the change of BL upon phenol addition.

As shown in FIGS. 5 and 6, the fact that the intensity of the biological light emitted from the bacteria is constantly kept prior to the addition of phenol is justification for judging that the bacteria is stably sustained in the second tank prior to the addition of phenol. In addition, the intensity was returned into the basic level in a short time after phenol addition.

Upon addition of phenol to 100 ppm, 300 ppm and 700 ppm in total, *E. coli* TV1061 emitted light of a maximum intensity in 30 min, 40 min and 55 min, respectively. Therefore, it takes 30–55 min to detect 100–700 ppm of phenol by use of *E. coli* TV1061 as a probe. As apparent, the time which it takes to reach the maximal intensity increases with phenol concentration. Phenol is an inhibitor against the growth of the probe, *E. coli* TV1061, so that the emitted light is attenuated upon phenol addition, but fresh bacteria are introduced from the first tank to the second bath. Thus, as phenol concentration increases, the recovery time is greater extended. For 1,400 ppm of phenol, the light intensity was rapidly decreased upon addition and returned to the preaddition level in 140 min.

As described hereinbefore, the bioreactor system using microorganisms as a toxicity probe, which comprises two separate two reactors, one supplying the probe in a lag phase to the other, can perform a probing performance continuously over an extended period of time. Since the system can be manufactured to be small in size, it is economically favorable. In addition, since the system according to the present invention can employ microorganisms which are adapted to luminesce upon reaction with toxic materials, it can be used to probe various toxic materials.

The present invention has been described in an illustrative manner, and it is to be understood the terminology used is intended to be in the nature of description rather than of limitation. Many modifications and variations of the present invention are possible in light of the above teachings. Therefore, it is to be understood that within the scope of the appended claims, the invention may be practiced otherwise than as specifically described.

What is claimed is:

1. A bioreactor system for detecting toxic materials comprising:
   a first-step reactor wherein microorganisms are continuously cultured in a constant phase, said microorganisms being genetically altered so as to emit light upon contact with at least one of a plurality of toxic materials;
   a second-step reactor wherein said microorganisms first contact said at least one of said plurality of toxic materials; and
   an optical detector optically connected to said second-step reactor;
   whereby, said microorganisms emit light which is transmitted to said optical detector.

2. The bioreactor system as set forth in claim 1, wherein said first-step reactor and said second-step reactor each have an operational volume of 57 ml or less.

3. The bioreactor system as set forth in claim 1, wherein said second-step reactor includes:
   a reactor tank;
   a water jacket surrounding said reactor tank having:
      a warm water inlet; and
      a warm water outlet;
   a magnetic stirring plate; and
   a media inlet and a media outlet whereby a nutrient media can be fed and drained from said tank;
   a drop wherein said microorganism and said toxic materials are continuously added to said tank;
   a gas pipe for discharging a gas resulting from a metabolism of said microorganisms;
   a condenser for cooling said gas prior to discharge;
   an air filter;
   an air conduit for introducing filtered air into said second-step reactor;
   a magnetic bar; and
   a glass window whereby said emitted light from the microorganisms is transmitted from said second-step reactor to said optical detector.

4. A bioreactor system as recited in claim 1, wherein said microorganism includes *E. coli* TV1061.

5. A bioreactor system for detecting toxic materials comprising:
   a first-step reactor wherein microorganisms are continuously cultured in a constant phase, said microorganisms being genetically altered so as to emit light upon contact with at least one of a plurality of toxic materials;
   a second-step reactor wherein said microorganisms first contact said at least one of said plurality of toxic materials; and
   an optical detector optically connected to said second-step reactor;
   whereby, said microorganisms emit light which is transmitted to said optical detector;
   said second-step reactor includes:
      a reactor tank;
      a waterjacket surrounding said reactor tank having:
         a warm water inlet; and
         a warm water outlet;
      a magnetic stirring plate; and
   a media inlet and a media outlet whereby a nutrient media can be fed and drained from said tank;
   a drop wherein said microorganism and said toxic materials are continuously added to said tank;
   a gas pipe for discharging a gas resulting from a metabolism of said microorganisms;
   a condenser for cooling said gas prior to discharge;
   an air filter;
   an air conduit for introducing filtered air into said second-step reactor;
   a magnetic bar; and
   a glass window whereby said emitted light from the microorganisms is transmitted from said second-step reactor to said optical detector.

6. A bioreactor system as recited in claim 5, wherein said microorganism includes *E. coli* TV1061.

7. A bioreactor system for detecting toxic materials comprising:
   a first-step reactor wherein microorganisms are continuously cultured in a constant phase, said microorganisms being genetically altered so as to emit light upon contact with at least one of a plurality of toxic materials;
   a second-step reactor wherein said microorganisms first contact said at least one of said plurality of toxic materials; and
   an optical detector optically connected to said second-step reactor;
   whereby, said microorganisms emit light which is transmitted to said optical detector;
   said second-step reactor includes:
      a media inlet and a media outlet whereby a nutrient media can be fed and drained from said tank;
      a drop wherein said microorganism and said toxic materials are continuously added to said tank; and
      a glass window whereby said emitted light from the microorganisms is transmitted from said second-step reactor to said optical detector.

8. A bioreactor system as recited in claim 7, wherein said microorganism includes *E. coli* TV1061.

* * * * *